United States Patent [19]

Walford

[11] Patent Number: 5,077,478
[45] Date of Patent: Dec. 31, 1991

[54] BASIS WEIGHT MEASURING SYSTEM

[76] Inventor: Graham V. Walford, 141 Newport Dr., Oak Ridge, Tenn. 37830

[21] Appl. No.: 563,565

[22] Filed: Aug. 6, 1990

[51] Int. Cl.$^5$ ............................................. G01N 23/06
[52] U.S. Cl. ............................... 250/359.1; 250/358.1; 250/308
[58] Field of Search .................... 250/308, 307, 336.1, 250/358.1, 359.1, 360.1

[56] References Cited

U.S. PATENT DOCUMENTS

| | | |
|---|---|---|
| 2,968,729 | 1/1961 | Pepper et al. . |
| 3,121,166 | 2/1964 | Vossberg . |
| 3,210,545 | 10/1965 | Barnett ................................ 250/308 |
| 3,412,249 | 11/1968 | Hanken .............................. 250/308 |
| 3,439,166 | 4/1969 | Chope .......................... 250/358.1 X |
| 3,757,122 | 9/1973 | Bossen et al. . |
| 3,761,712 | 9/1973 | Listerman . |
| 3,889,121 | 6/1975 | Bossen . |
| 3,914,607 | 10/1975 | Cho et al. ............................ 250/308 |
| 4,037,104 | 7/1972 | Allport . |
| 4,147,931 | 4/1979 | Puumalainen . |
| 4,155,009 | 5/1979 | Lieber et al. ........................ 250/308 |
| 4,208,581 | 6/1980 | Kaneko ........................... 250/308 X |
| 4,301,366 | 11/1988 | Bertin et al. . |
| 4,574,194 | 3/1986 | Coats et al. ......................... 250/308 |
| 4,599,514 | 6/1986 | Cho .................................. 250/359.1 |
| 4,845,730 | 7/1989 | Mercer ........................ 250/359.1 X |
| 4,920,265 | 4/1990 | Chase et al. ......................... 250/308 |
| 4,979,197 | 12/1990 | Troxler, Sr. et al. ................ 378/90 |

Primary Examiner—Constantine Hannaher
Assistant Examiner—Edward J. Glick
Attorney, Agent, or Firm—Pitts & Brittian

[57] ABSTRACT

An improved basis weight measurement system which utilizes two means for irradiating a material to determine the distance from the radiating device to the material being surveilled and its mass per unit area. A portable, self-contained device applying this principle contains first and second radioactive emission means with corresponding detectors for each. A weaker emission is reflected back from the surface of the material to a detector, and a backscattered portion of a stronger emission is received by a detector after having penetrated the material. By virtue of there being two separately detectable emissions, the device can be used proximate the material being measured in order to perform the measurement without the need for direct contact between the device and the material. The measured basis weight is read directly from a digital Liquid Crystal Display, with the distance between the device and the surveilled material being indicated by Light Emitting Didoes. Another feature of the dual irradiation property of the device is that the speed of movement of the material does not deteriorate the accuracy of the measurement. Electronic memory and interface means are also provided for later transfer of data to a base computer and/or printer.

13 Claims, 6 Drawing Sheets

BASIS WEIGHT MEASURING SYSTEM

TECHNICAL FIELD

The system of the present invention relates generally to radiation backscatter systems for measuring the density/thickness per area measurement of sheet material, known as a basis weight measurement, and more especially concerns a system for making such measurements. When incorporated in the example instrument in this invention it makes the measurement without contact with the material under test and provides visible indications of the result. It is also possible to measure the density of a material having a thickness greater than the penetrating ability of the radiations selected. The technique allows noncontacting backscatter measurements to be made and can provide compensation for the movement of the material under test, or of the device, while the measurement is in progress.

The technique described herein can be added to transmission gauge devices to provide compensation of errors caused by the "flutter" (unwanted motion) of the material under test in transmission gauges.

BACKGROUND ART

Devices operating on principles similar to the present invention have been known and used heretofore. Known prior art concerned is described in U.S. Pat. No. 3,757,122, granted to Bossen, et al; number U.S. Pat. No. 2,968,729, Pepper, et al; U.S. Pat. No. 3,889,121, Bossen; U.S. Pat. No. 3,761,712, Listerman; U.S. Pat. No. 3,121,166, Vossberg; U.S. Pat. No. 4,147,931, Puumalainen; U.S. Pat. No. 4,037,104, Allport; and U.S. Pat. No. 4,301,366, Bertin, et al.

The Basis Weight Gauging Apparatus, System and Method of Bossen, et al, '122, utilizes a fixed immobile installation having separate heads for radiating and detecting with a spaced relationship therebetween, and requires that a prior measurement of a representative sample of the material be supplied. This non-portable device makes no provision for measuring and/or compensating for the distance between radiating/detecting heads and the material.

The device of Pepper, et al, '729, also requires the use of a representative sample of the material being measured. This device further requires the use of two ionization chambers, together with a bi-directional emissivity pattern of the radiating material, one lobe of which is constantly irradiating the sample as a reference standard. A difference-derived signal is employed to drive a motor which varies an aperture controlling the amount of radiation applied to the material being measured. A mechanically coupled gauge provides an indication of the thickness/density of the material. It would appear that this device would not be well-adapted for portability, and there is no provision for measuring and/or compensating for the distance between radiating-/detecting heads and the material.

The device described by Bossen in U.S. Pat. No. 3,889,121 utilizes beta and X-Ray radiating materials but is expressly designed for the particular situation of its described embodiment, wherein a core made of a specific material, such as steel, is overlaid with a dissimilar material, such as rubber. This device must also be calibrated with a series of representative samples of the material(s) to be measured. There is no provision made for measuring and/or compensating for the distance between the radiating/detecting heads and the material. Bossen's claims are for: "1. An apparatus for measuring the weight per unit area of various constituents of a tire fabric manufactured by calendering rubber onto both sides of a metal cord, comprising...", and "9. Apparatus for measuring the weight per unit area of a manufactured sheet product consisting of a first material layer having a first scattering or absorption characteristic and a second material layer having a second scattering or absorption characteristic and wherein said first characteristic is different from said second characteristic, said apparatus comprising:...". The limitations of a tire fabric and first and second material layers clearly distinguish this device from that of the present invention which is generally intended for all types of sheet materials.

The device of Listerman, '712, although utilizing a source for both neutron and gamma radiation, is for a moisture gauge to determine the moisture content of bulk substances and not a density/thickness measurement device.

The non-portable device of Vossberg, '166, designed and intended for use particularly in measuring the volumetric contents of a series of sealed cans, has no provision for measuring and/or compensating for the distance between the radiating/detecting heads and the material. His claim is for a method of alternating between two sources or power levels of radiation to irradiate one side of a specimen to be measured.

Puumalainen, '931, teaches a device for measuring the unit area weight of a coating on paper by first coating it with a pre-coat. This device is said by its inventor to require 10-20 seconds to achieve a measuring accuracy of +0.5 grams per square meter. This would appear to impose a severe limitation on the possible flow rate of the material to be measured. Further, this device does not directly indicate any weights but only provides an indication from which the weight of the coating is calculated.

Allport, '104, teaches a device for measuring the thickness of ferrous and nonferrous metals, specifically. This device uses radiation sources on one side of the material and detectors on the other side, requiring that both sides of the material be accessible. Allport's purpose in this invention is to compensate for changes in the composition of a sheet of metal alloy without affecting the usefulness of the device to monitor the thickness thereof.

The device of Bertin, et al, '366, is designed to detect a special kind of thickness variation, called "chatter," which is peculiar to cold rolled steel.

The devices just described above encompass many applications of the art of measuring sheet materials through the use of radioactive emissions and the reflections thereof. However, such prior art devices have failed to provide a backscatter gauge which is portable and usable under unlimited environmental conditions, and wherein only one side of the material to be measured must be accessible. Furthermore, such prior art devices have been subject to errors introduced by such factors as movement of the material being measured, obscuration of emissivity windows, aging of the radioactivity emitters, etc.

Accordingly, it is a principal object of the present invention to provide an improved basis weight measurement system utilizing any of a variety of devices which can make such measurements without the need for direct contact with the material being measured.

It is another object of the present invention to provide such an improved basis weight measurement system utilizing devices which can make such measurements without being affected by movement of the material being measured.

It is a further object of the present invention to provide such a basis weight measurement system utilizing devices which may be used in either fixed immobile, fixed mobile (scanning), or portable applications.

It is still another object of the present invention to provide such a basis weight measurement system utilizing devices which can employ any combination of alpha, beta, gamma, and/or X-Ray radiation, or high and low power combinations of such radiation emitters to effect such measurements.

It is yet a further object of the present invention to provide such a basis weight measurement system utilizing devices which will supply identification data to uniquely and individually identify each measurement made.

It is still another object of the present invention to provide a such a basis weight measurement system utilizing devices which can be substantially self-calibrating.

These and other objects and advantages of the present invention will become readily apparent from the following detailed description, when taken together with the accompanying drawings.

DISCLOSURE OF THE INVENTION

In accordance with the present invention, there is provided a portable backscatter gauge as an exemplary device for illustrating the system of the present invention, which is the measuring of the thickness and/or density (basis weight) of a sheet of material, utilizing two sources of radioactivity emission. A more penetrating of the two radioactive emissions substantially penetrates the material being measured and yields a backscattered remnant which is measured to indicate the density of the material by comparing the value with an internally stored empirical calibration. The less penetrating of the two radioactive emissions, reflecting directly from the surface of the material, is used to indicate the distance (or more expressly the solid angle "coupling" of the source-material-detector geometry) between the gauge head and the sheet material being measured. In this manner, the device of the present invention is made immune to both the need for making comparative measurements with a reference sample of the subject material, and the errors introduced by aging of the emitting material, and/or variations in distance and relative motion between the two.

Measurements of sheet material of interest can be made as though taking a series of rapid snapshots which are recorded in memory, with each measurement being given a unique identification tag, together with the date and the time of day at which the measurement was made. A visual indicator informs the operator when the device is within optimum distance parameters from the material being measured.

BRIEF DESCRIPTION OF THE DRAWINGS

The following drawings illustrate a preferred embodiment of the invention and, when taken together with the accompanying description, serve to explain the principles and structure of the invention.

BEST MODE FOR CARRYING OUT THE INVENTION

Figure 1:
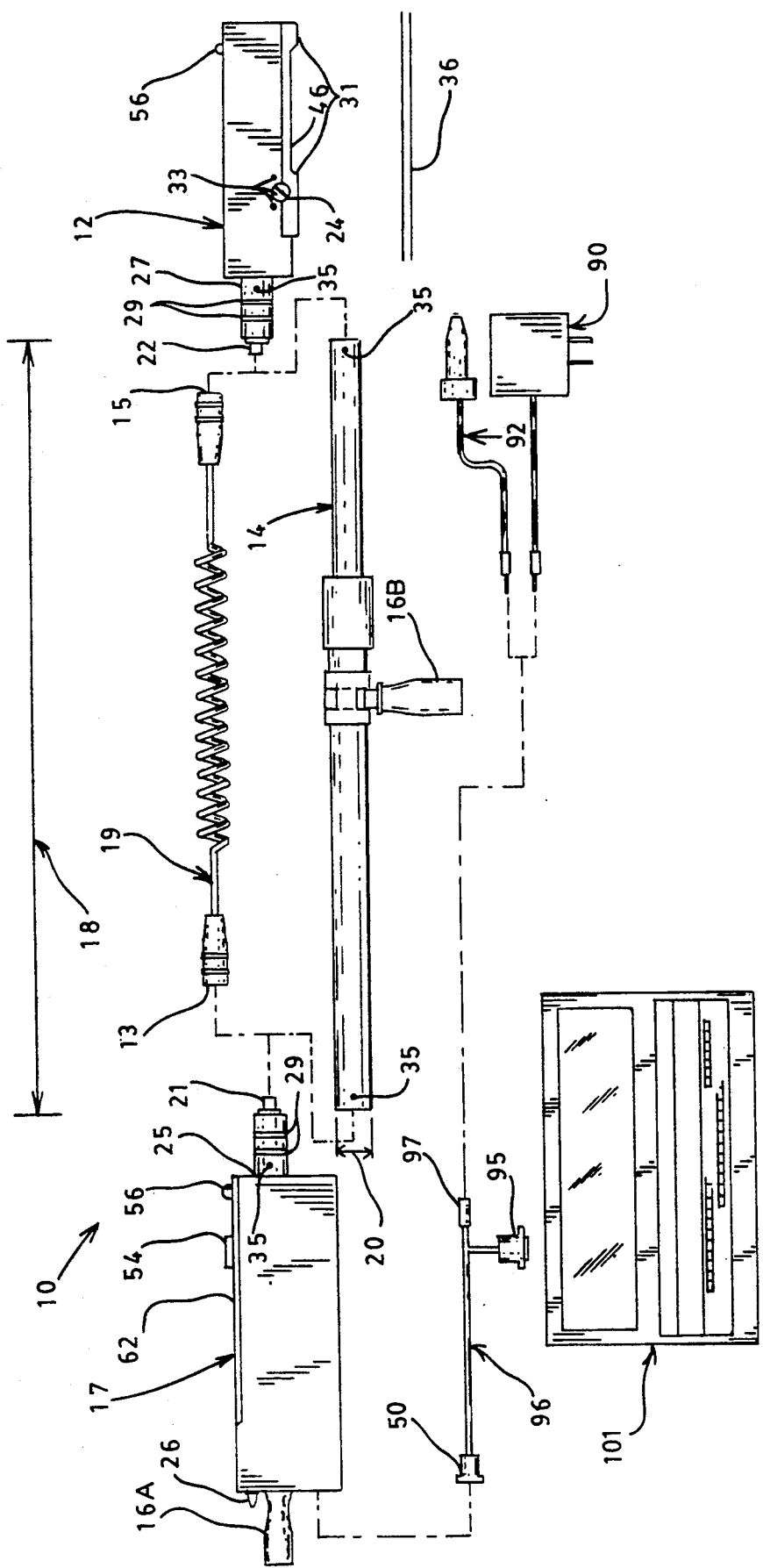
FIG. 1 is a drawing of the component parts of a device constructed in accordance with various features of the present invention

The following description can be best understood by referring to the accompanying drawings, wherein like numerals designate like parts. Beginning the description by referring specifically to FIG. 1, a portable backscatter gauge is designated generally at 10 as an exemplary device for illustrating the principles of the system of the present invention.

The components of the device 10 are distributed between two major assemblies, a gauge head 12 and a processor housing 17, with a hollow support shaft 14 connecting the two. A coiled-tension, flexible cable 19 passes through support shaft 14 to provide electrical connections between gauge head 12 and processor housing 17. Electrical connectors 13 and 15, located at each end of cable 19 and covered with rubber "boots", plug into sockets 21 and 22 which are hermetically sealed at their interfaces with the interiors of housing 17 and head 12, making a completely watertight connection at both ends. Physical connection and strength is effected by inserting welded extensions 25 and 27 of housing 17 and head 12, respectively, into the ends of shaft 14. Extensions 25 and 27 are closely machined to provide a tight fit within the shaft 14. O-rings 29 on extensions 25 and 27 complete the fit by making them waterproof, also. Finally, pins are removably driven through extensions 25 and 27 at the points marked 35 so as to make it impossible to accidentally disconnect head 12 or housing 17 from shaft 14.

Support shaft 14 provides a means for an operator to support the gauge head 12 at a minimum distance of twenty inches from the processor housing. Shaft 14 can be made of any suitable material of a length 18 and diameter 20 to suit the particular environment in which it is to be installed or utilized. For instance, in a preferred embodiment, shaft 14 can be fabricated from one or more tubular lengths of aluminum, or such like material, of a diameter 20 of ⅜", for example, and a length 18 of twenty inches. Of course, other similar materials could be employed as well as aluminum, such as polyvinyl chloride (PVC), for instance, the primary considerations being strength, rigidity, and weight, with the most strength and rigidity for the least weight being the desired criteria for portable applications.

Further, shaft 14 can also be comprised of more than one section arranged in one of the configurations well-known in the art, such as telescoping, for instance, for the purpose of extending the gauge/detector head 12 out to a greater length 18, such as forty inches, for example. Shaft 14 can also be provided with a handle, such as that designated 16B. Handle 16B can also be made of any appropriate material, shape, and size, and can be of the embodiment described or some other arrangement. In the described embodiment, handle 16B is fixedly attached to support shaft 14 so as to extend therefrom at a substantially right angle in such a manner that it can swivel around shaft 14, as well as up and down, and lock in any position.

Figure 2A:
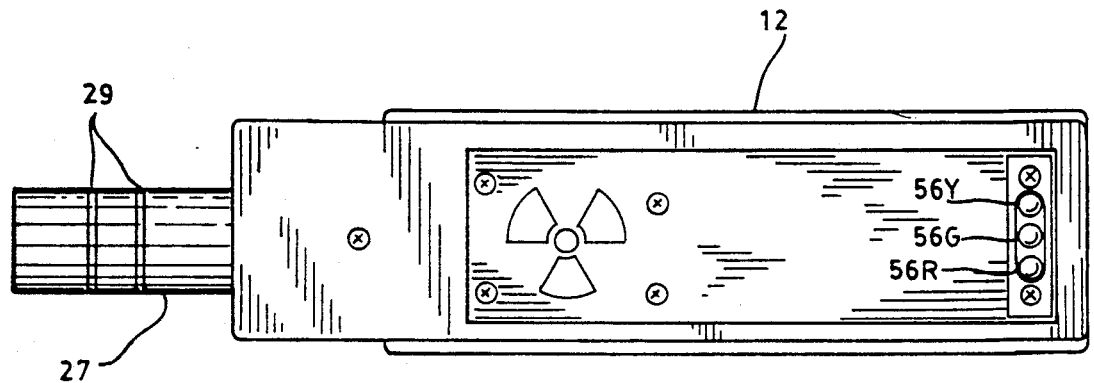
FIG. 2A is a drawing of a top view of a gauge head portion of the device of FIG. 1.
Figure 2B:
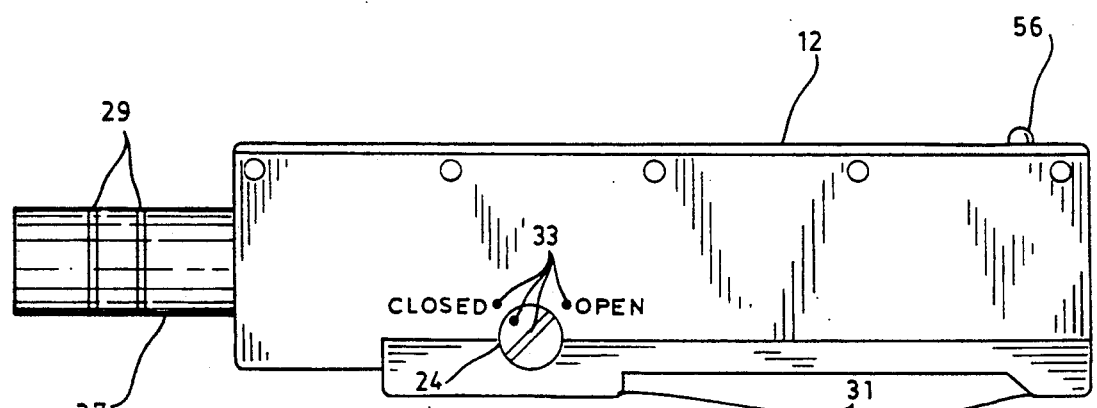
FIG. 2B is a drawing of a side view of a gauge head portion of the device of FIG. 1.
Figure 2C:
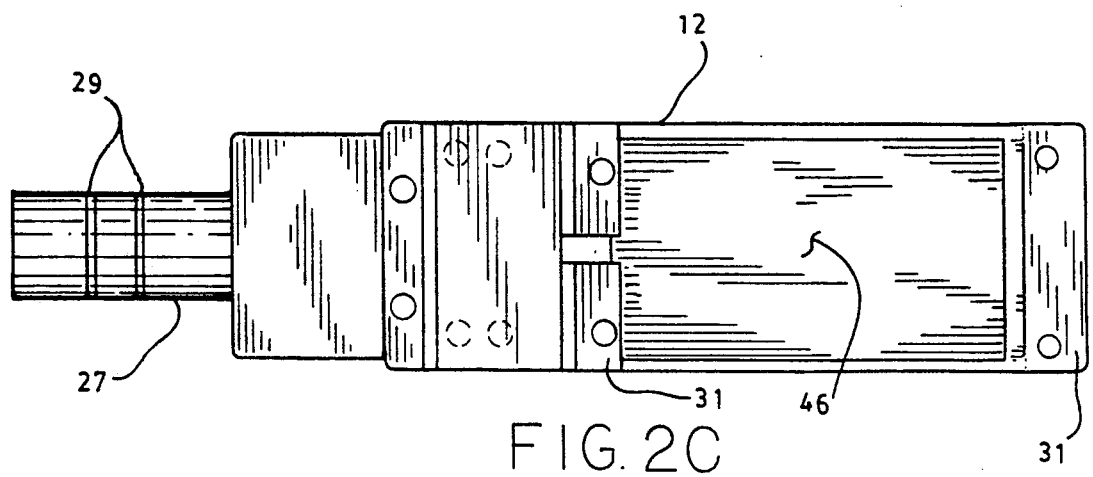
FIG. 2C is a drawing of a bottom view of a gauge head portion of the device of FIG. 1.
Figure 2D:
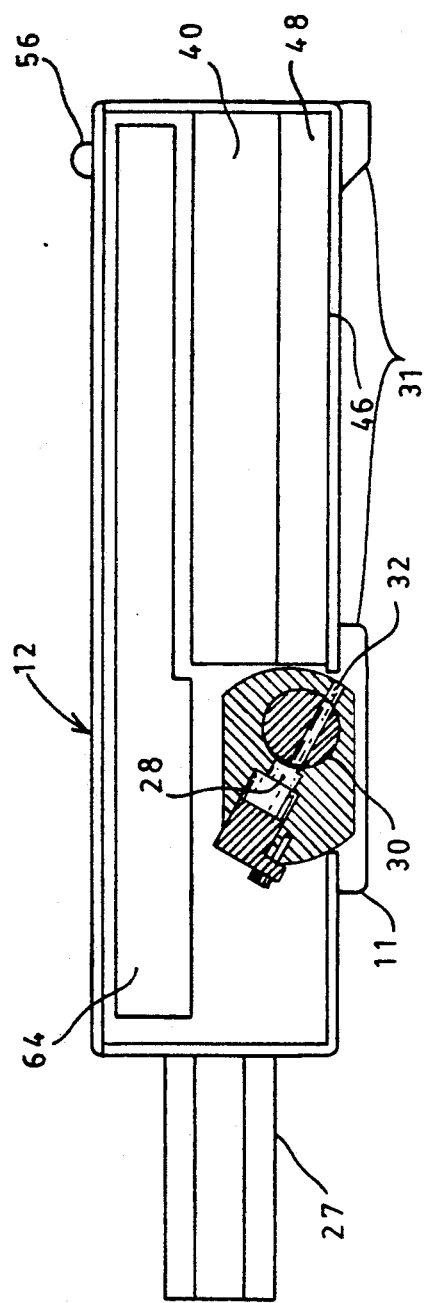
FIG. 2D is a drawing of a side view of a gauge head portion, partially in section, of the device of FIG. 1, showing a radioactive source container and closed shutter.
Figure 2F:
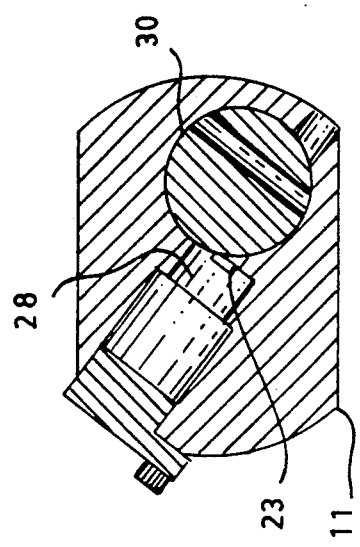
FIG. 2F is a drawing of a radioactive source container, in section, with a shutter portion thereof shown closed.
Figure 2E:
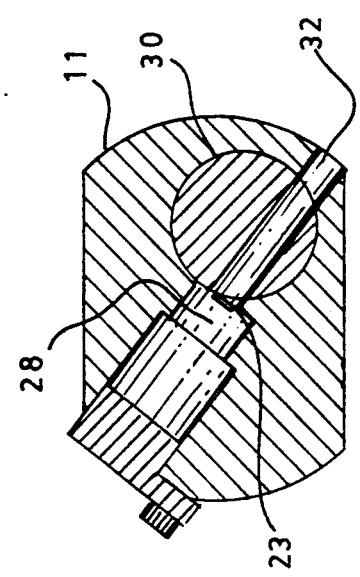
FIG. 2E is a drawing of a radioactive source container, in section, with a shutter open.

The gauge head 12 is a hermetically sealed case made of 0.125" thick aluminum in the described embodiment. On the bottom surface, protrusions called skids 31 can be provided for buffering any contact with a material 36 under surveillance. A thin sheet of stainless steel, called a window 46, can be mounted in the space between the skids 31. Distance indicating LEDs 56 can be mounted on an upper surface of gauge head 12, as shown. A knob 24 can be provided for rotating a shaft to open and close a shutter 30 (FIGS. 2B, D, E, and F) through the side of gauge head 12. Shutter status indicating means 33 can be provided on the knob 24 and the side of gauge head 12 to show at a glance whether the shutter 30 is open or closed. In a preferred embodiment, the opening in the sidewall of head 12 for the shaft of knob 24 is provided with a hermetic seal and bearing means.

The gauge head 12, which is shown in greater detail in FIGS. 2A-F, contains the source(s) of the radioactive emissions at a mounting 28, the detectors 40 and 48 for detecting the emissions returned from the material 36. Also, there is a unit including signal conditioning electronics, a battery power pack, and a power supply for powering the electronics within a hermtically sealed unit 64.

One or more sources of radioactivity, one of which can be designated 76 and the other 82 (see FIG. 4), can be mounted at 28 within a shielding enclosure 11, which can be made of tungsten, for instance, as illustrated in FIGS. 2D-F and 3. A shield/ shutter 30, having an opening 32 and capable of being rotated approximately 90 degrees, can be provided in front of a radiation source at 28 to complete the shielding thereof. Shutter knob 24 can be affixed to a shaft, as previously described, attached to a shutter 30, for mechanically rotating the shutter 30 from its normally closed position to a position in which opening 32 is placed in front of radiation source 28. This action allows radiation from the source at 28 to be emitted along opening 32 and out to irradiate a material 36. A detent can be provided to hold shutter 30 in the open position. Reversing shutter knob 24 allows the spring-biased shutter 30 to return automatically and positively to the closed position.

A detection device for each of the radiation types is also contained in gauge head 12. X-Ray (or lower energy level) radiation backscatter radiates back from material 36, passing through stainless steel window 46 and through the beta detector 48 to X-Ray detector 40, which converts it into an electrical signal. The strength of the electrical signal is directly proportional to the relative strength of the received signal; therefore, the weaker the backscattered signal received, the greater the density (or thickness) of the material 36 being measured. The electrical signal so created is conducted to the basis weight channel of the electronic signal conditioning circuitry shown in the block diagram of FIG. 3.

Beta particles (or higher energy level radiation) emitted through collimator opening 32 are reflected back from the surface of material 36, through window 46, and onto plastic beta detector 48. Beta detector 48 converts the received particles into an electrical signal indicative of the relative strength of the received signal; therefore, the weaker the reflected signal received, the greater the distance between the gauge head 12 and the material 36 being measured. This electrical signal is routed to a distance channel of the signal conditioning electronics illustrated in FIG. 3. This signal can serve to illuminate the appropriate one of Light Emitting Diodes (LEDs) 56 to indicate distance conditions to an operator. In a preferred embodiment, three LEDs 56 are provided on gauge head 12 as can be seen in FIGS. 1 and 2A, 2B, and 2D. A yellow LED, 56Y, can indicate by its illumination that the gauge head 12 is too far away from the material 36 being surveilled. The opposite condition, that of the gauge head's being too close to material 36, could be indicated by the illumination of a red LED 56R. An optimum separation distance, between one and three inches, could be indicated by the illumination of a green LED 56G. These electrical signals will be described in more detail in a following portion of this description.

Figure 3:
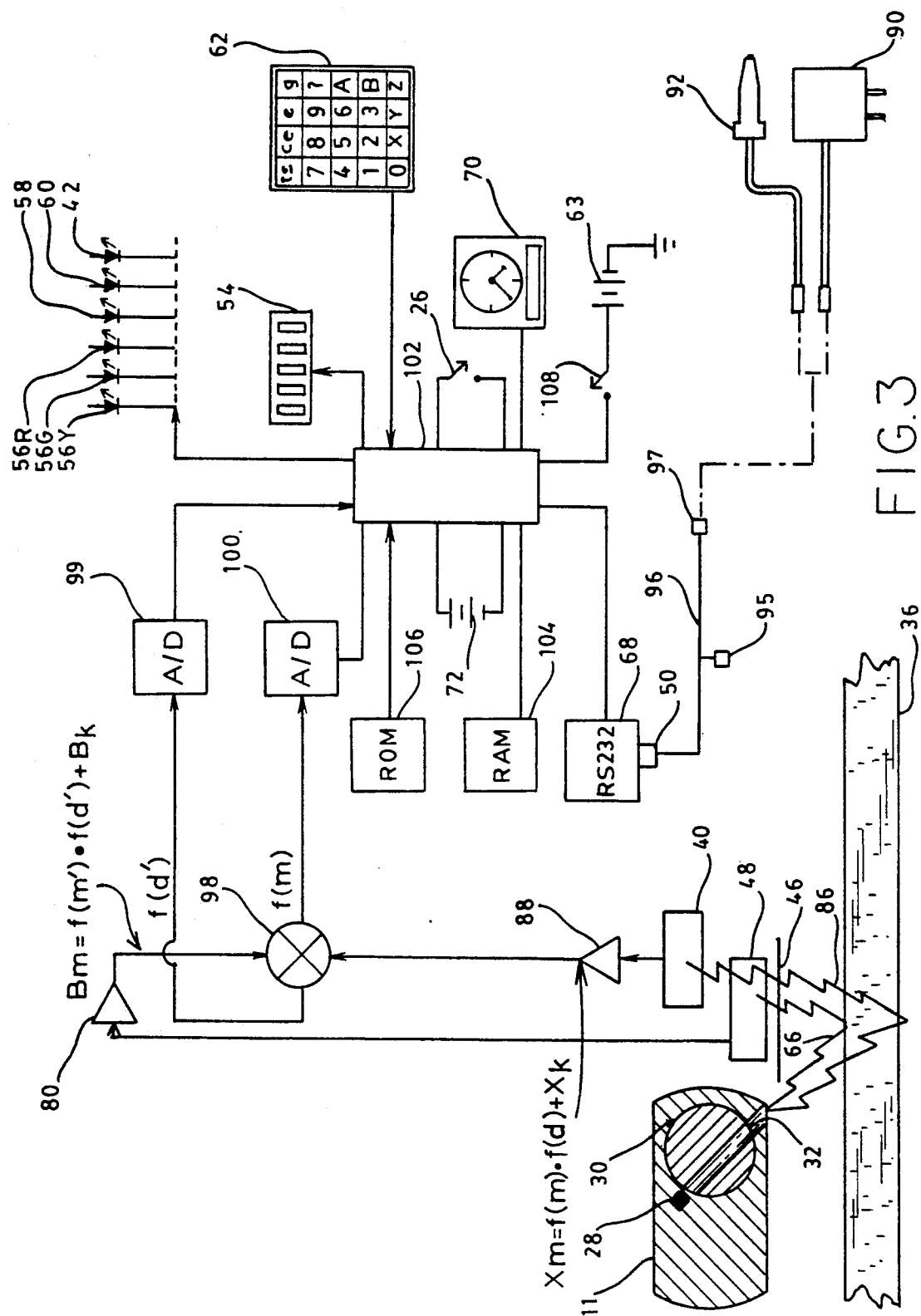
FIG. 3 is a block diagram of the electronic circuitry of the device of FIG. 1.

In a preferred embodiment, the gauge head 12 can also carry the electronic signal conditioning circuitry, a block diagram of which is shown in FIG. 3. This circuitry can be powered by a DC supply and a rechargeable battery 63, which can be recharged from an AC source by an external charger 90 connected through connector 97, cable 96, and connector 50 to RS-232 68. An adapter 92 can be supplied to charge the battery 63 from the battery of an automobile through the cigarette lighter fixture thereof.

The radioactive emissions detected by the two detectors 40 and 48 are converted into electronic signals, one representative of distance, and the other representative of basis weight measurement. These two signals are routed through the flex cable 19 to the electronic data processing circuitry contained in processor housing 17.

Also contained within gauge head 12 are the returned radiation detectors 40 and 48. Beta detector 48 is located just above the stainless steel window 46, which is 0.001" thick. Just above detector 48 is located X-Ray detector 40. Beta detector 48 is a plastic scintillator, while X-Ray detector 40 is comprised of a half-inch thick layer of sodium iodide. Each of these detectors converts the radiation it receives into an electrical signal which is coupled into the signal conditioning electronics. 1500 Volt and 7.5 Volt power supplies are contained in gauge head 12, along with a rechargeable battery pack 64, for powering the electronics.

In the preferred embodiment, when knob 24 is rotated to open shield 30 and allow the material 36 to be exposed to the radiation of a source at 28 through collimator/opening 32, two types of emissions from a single source will be emitted to irradiate material 36, with the returns therefrom detected by the detectors 48 and 40. This dual radiation phenomenon occurs when some of the beta radiation, emitted by the source at 28 and travelling through the collimator/opening 32, strike atoms of the tungsten of which shutter 30 is composed and generate X-Ray radiation thereby. Both the X-Rays and other beta emissions will continue down collimator 32 to strike the surface of material 36, the beta emissions being reflected directly therefrom. These beta emissions, reflected back to gauge head 12, will pass through a window 46 of stainless steel, no more than 0.001" thick, to reach plastic beta detector 48, within which these emissions are converted into an electrical signal containing functions of both the distance between gauge head 12 and material 36, and the density of material 36, together with a natural condition constant.

At the time that the beta particles are being reflected from the surface of the material 36, the X-Rays are penetrating the same material 36, generating a backscattered result of the interaction between the X-Rays and the atoms of material 36. This backscatter not only goes through the stainless steel window 46 just as the beta did, but it also passes right through the plastic beta detector 48 before it arrives at X-Ray detector 40. Here, it, too, is converted into an electrical signal, containing functions of both the distance and density factors, together with an inherent constant.

Although it is one feature of the present invention that two different radiation sources, 76 and 82, can be used to make the desired measurements, it is a preferred embodiment that gauge head 12 contains only one source of radioactive emissions 76, mounted at 28. This source of radiation can be an isotope of Strontium-90 ($^{90}$Sr), Americium-241 ($^{241}$Am), and/or Krypton-85 ($^{85}$Kr), for example. In this application, one of the emitters, such as $^{85}$Kr, for example, can be a source of beta particles while the other, such as $^{90}$Sr, can emit X-Ray radiation.

It is an important alternate embodiment of the system of the present invention that one radioactive material, such as either of the types just above mentioned, for instance, can serve as a source of both beta and X-Ray radiation. This feature makes use of the principle of bremstrahlung. Briefly stated, the principle of bremstrahlung generation is the name given to the effect which occurs when beta radiations interact with the material they are in to produce X-Rays, for instance, strike atoms of a material, such as tungsten, for instance, and thereby lose some of their energy, converting the radiation type from beta radiation to X-Rays and lower energy beta particles.

The foregoing principle is used to great advantage in the system of the present invention. The amount of bremstrahlung generated is a function of the beta radiation, incident energy, and the atomic number of the material being irradiated. The higher energy beta radiation will produce higher energy X-Rays and with higher intensity. Higher atomic number materials, when irradiated with beta particles, will produce greater generation of X-Rays with higher energy when compared with lower atomic number materials. The combination of appropriate beta source selection and collimator materials allow optimum radiation safety shielding design while controlling the intensity of the beta radiation and energy, as well as the intensity of the X-Rays generated.

A major advantage of using X-Ray (bremstrahlung) generation from a beta source as the penetrating radiation in a measurement is that the beta emission from the source and the X-ray generation will share similar irradiation geometries and therefore similar distance functions.

The approach described above provides a specific and separate measurement of the beta (or distance function) and X-Rays (the mass measurement). It is possible to use one detection element if it is sensitive to both radiations selected for the measurement and can separate them by energy resolution capability and/or pulse shape discrimination.

Thus, one type of radioactive material can suffice as a source of two types of radiation, one of which can be used to monitor and indicate the distance between a radiating source and a material being irradiated, the other of which can be used to indicate the basis weight of such a material. In the device of the present invention, a pellet of aluminum 23 (see FIGS. 2E and 2F) is located in the shield/shutter 30 so that, in the closed position, the radiation flux is incident upon this pellet 23 rather than the tungsten of shutter 30 so as to minimize the generation of undesired Bremstrahlung.

Another functional feature of the system of the present invention comprises the use of higher and lower energy levels of a single radioactivity emitter instead of the described method of two types of radiation, such as beta and X-Ray, to determine both the distance and the density factors.

Figure 4:
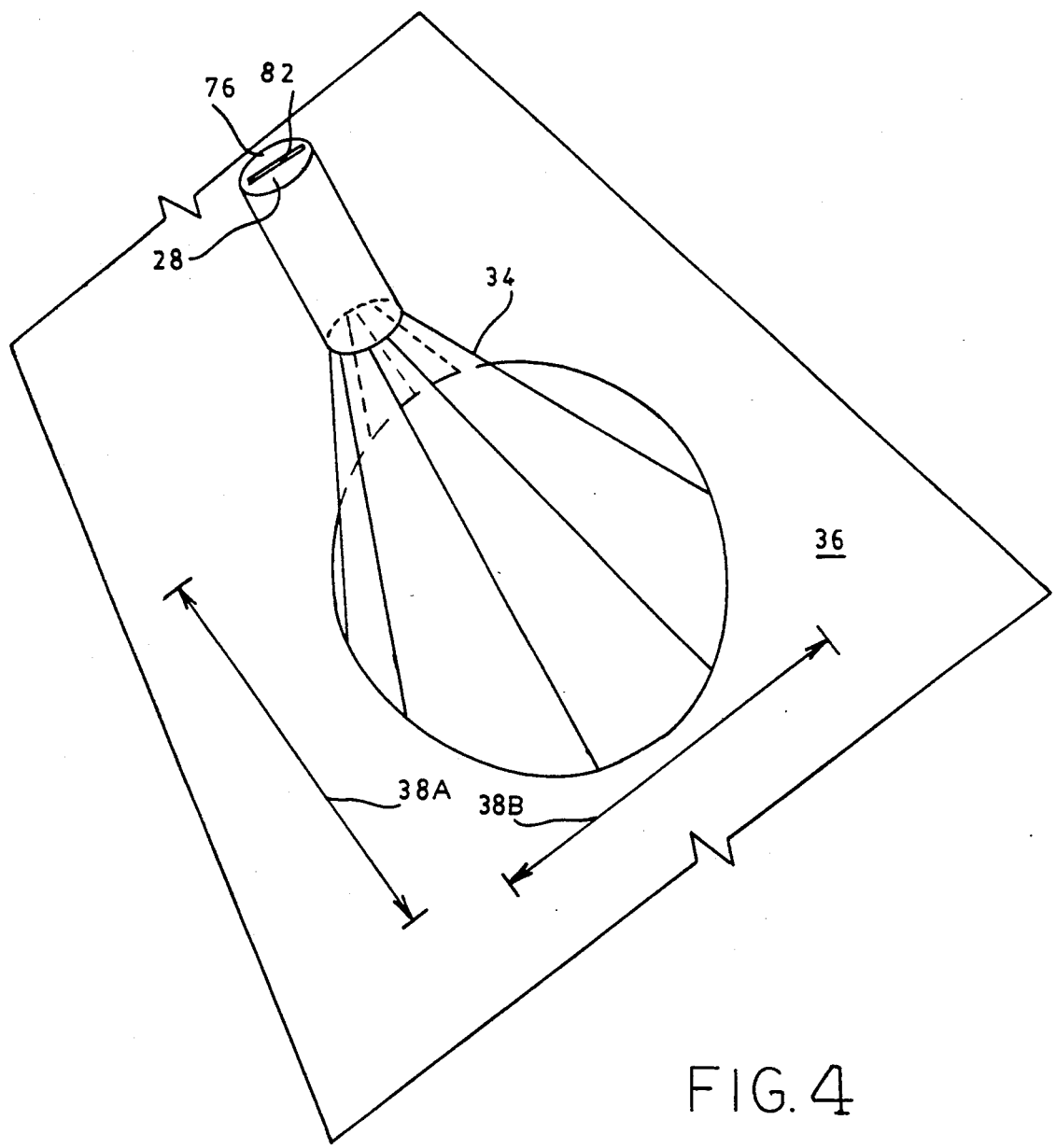
FIG. 4 is a detailed drawing of the solid angle of radiation.

If two sources 76 and 82, FIG. 4, of radioactivity are used, they are preferably mounted in parallel and in close proximity to each other at 28 within a rotating tungsten shield 11, with a shutter 30 having a collimating opening 32 for directing the output of the emitting devices at a selected solid angle of irradiation 34 onto a sheet of material 36 to be surveilled. This solid angle of irradiation 34 also forms an important part of the system of the present invention. This solid angle of irradiation 34 must be of appropriate size and angular relationship with respect to the gauge head as to irradiate a sufficient quantity of material, so that returning signals are of usable strength. The amount of material 36 exposed to radiation is that area of material 36, indicated by arrows 38A and 38B, covered by the solid angle of irradiation 34. If two radioactivity sources, 76 and 82, are used, they must be mounted so that their respective solid angles of irradiation 34 are substantially identical, ensuring that substantially the same area of material is simultaneously irradiated by each source. Of course, the area irradiated increases approximately with the square of the distance between the gauge head 12 and material 36, while the signal strength diminishes at substantially the same factor. Further, the angle at which the gauge head 12 is positioned relative to material 36 will be seen by those skilled in the art to be similarly important in affecting the quality and strength of the returned signals.

A processor housing 17 can be located at the opposite end of shaft 14 from gauge head 12. The case for processor housing 17 can be fabricated and hermetically sealed in a manner similar to that of gauge head 12 so as to also be impervious to the entry of dust and moisture. A handle, such as the one shown at 16A, can be attached to an end of processor housing 17 distal from shaft 14.

Preferably, the upper surface 62 of housing 17 can contain input/output controls and indicators, (see FIG. 3) such as a multidigit LCD readout 54 (or equivalent), LEDs 56 for indicating distance, valid data 60, satisfactory data storage 58, low battery 42, etc., and switches, one for applying power 108, and one for storing data 26, for instance.

In a preferred embodiment, processor housing 17 can contain data processing electronics, rechargeable batteries 72, and an RS-232 communications port 68. Cable 19 conducts signals and some power from gauge head An operator's entry keypad 62 for labeling, or "tagging," each measurement for identification can also be provided on the face of processor housing 17. Keypad 62 can be one of the types well-known in the art, or of a design particularly arranged to suit the device 10 of the present invention. One of the functions of keypad 62 is to provide a unique identification to each measurement made and stored in the electronic memory of the device 10. The style of keypad 62 illustrated can provide a plurality of different identifying tags which, when entered with the time of day and the date, can yield an unambiguous identification of each measurement taken.

The data processing portion of the present invention, mounted in the processor housing 17, is comprised generally of standard components and circuits well-known in the electronics art for processing and storing data. An RS-232 (or other protocol) interface 68, FIG. 3, can be provided, as well as a clock/calendar circuit 70, to supplement operator input means 62 for applying identifying "tags" to specific readings, together with look-up data table(s) and a program of instructions stored in read only memory (ROM) 106. The liquid crystal display 54 is mounted on the face of the processor housing 17, as is a parallel set of three distance indicating LEDs 56, identical to those on the gauge head 12. The internal programs and look-up tables stored in ROM 106 can be protected by an internal battery 72, such as a ten year lithium battery 72, for instance.

In the following description of the operation of the electronic circuit portion of the present invention, it is understood that energizing power has been applied by on/off switch 108, that the operator has entered via keypad 62 an identifying tag for the measurement to be made, and has operated shutter knob 24 to rotate the shutter 30 to the open position, thereby releasing radiation from a source of radioactivity at 28 onto material 36.

It can be seen in the block diagram of FIG. 3 that a radiation source at 28 emits a beam of radiation 66, assumed to be beta for the purposes of this illustration, which strikes material 36 at a solid angle of irradiation 34 (shown in FIG. 4), and is reflected back to beta detector 48. This signal, being reflected from the surface of material 36, is representative of the distance between the gauge head 12 and the material 36. The reflected radiation absorbed by detector 48 causes an electronic signal to be generated therein, which is then conducted to one or more stages of amplification 80 in the distance channel.

A second type of radiation at 28 is emitted as represented by beam 86, penetrating material 36 instead of being reflected back from it. A backscattered atomic agitation resulting from this penetration of material 36 is detected by X-Ray detector 40. This return of the second radiation type is converted into a second electronic signal, representative of the basis weight of material 36, by X-Ray detector 40, from the output of which the second signal is conducted to one or more stages of amplification 88 in the basis weight channel.

From amplification stages 88 and 80, the amplified basis weight and distance information signals, represented by their mathematical relationships $Xm = f(m) * f(d) + Xk$ and $Bm = f(m') * f(d') + Bk$, respectively, go to a resolver circuit 98. Resolver circuit 98 removes the distance factor f(d) from the basis weight channel, and the basis weight factor f(m') from the distance channel, together with the constants Xk and Bk, leaving a distance signal f(d') and a basis weight signal f(m).

Distance signal f(d') is converted into digital bits in Analog to Digital Converter 99, after which the bits are sent to microprocessor 102. Microprocessor 102 reacts to the intelligence contained in the distance signal by illuminating the appropriate LED to indicate to an operator the relative distance between the detector head 12 and material 36. The illumination of yellow LED 56Y indicates that the distance is too great for a reliable measurement to be made, and the red LED 56R indicates that the distance is too small. Of course, green LED 56G indicates that the distance is within the optimal zone for making a reliable measurement.

The basis weight signal derived in resolver circuit 98 goes to an Analog to Digital Converter 100 from which it, too, emerges as a string of digital bits which proceeds on to microprocessor 102. The microprocessor 102 assimilates the basis weight data signal with the inputs from keypad 62 and the clock/calendar circuit 70. When all appropriate preset conditions have been satisfied, microprocessor 102 generates a signal to illuminate the valid data indicator LED 60. When an operator sees that LED 60 has been illuminated, he operates data storage switch 26, transferring the digital bits being held by microprocessor 102 into random access memory (RAM) 104 for long-term storage while simultaneously displaying the determined basis weight of material 36, converted into engineering units, on display 54. When the data have been satisfactorily stored in RAM 104, microprocessor 102 flashes LED 58 to indicate to the operator that a satisfactory data save has been accomplished. Subsequently, the data saved in RAM 104 can be down-loaded via interface 68 through connector 95 to an external computer 101, for example, or a printer, or other such device (none shown) as desired.

Of course, other indicating methods and devices, such as gauges, gas counters, silicon detectors, scintillators, or detectors of differing atomic numbers and sensitive to thickness, for instance, can be employed with devices using the system of the present invention, and the embodiment described is simply one exemplary possibility. Furthermore, a sonic, Doppler, or optic device, such as a laser light generator, for example, can be employed, alone or in conjunction with other devices, in determining the device-to-material distance instead of a form of radiation.

It will be seen by those skilled in the art that, in addition to the portable embodiment described, the device 10 of the present invention can also be applied in other environments, such as a fixed, immobile installation, in which detecting head 12 can be installed on a bracket, for example, proximate the flow of a mass of material 36 to be measured. In this embodiment, the data are sent to some more or less distant monitoring point instead of going to an indicator of an instrument held by an operator. Of course, such an embodiment can also include installation in a fixed, mobile environment, such as a scanning head, for instance, wherein the detector head 12 of the present invention 10 is made to continually pass back and forth transversely over a mass of material 36 to be monitored/measured. The data derived from such installations could be sent to one or more of the monitoring/recording devices well-known in the art, such as gauges, chart recorders, or lights, for example, or in a closed loop circuit to continuously vary the composition of the sheet material to maintain a predetermined thickness/density. Further, the system of the present invention can also be employed in arrangements where the device containing the emitting agent is located on one side of a material to be measured, and a detector device is located on the other side of such material.

Prior to making a measurement, in the portable embodiment being described, an operator should enter, via keypad 62, the tagging data chosen to identify the particular measurement about to be made. Then, when knob 24 and switch 26 are both operated, the data generated by the returned signals will be stored in memory, together With the identification tag, the date, and the time of day at which such measurement was made.

In use, the detector head 12 of device 10 is optimally positioned between one and three inches above a sheet of material 36 to be measured, at which time knob 24 is rotated to rotate shutter 30 and expose a radiation source at 28. The rotation of shutter 30 allows the radiation source at 28 to irradiate the material 36 at a common solid angle of coupling through the collimator 29 located in window opening 32. If the device 10 is too close to the material 36, the red LED 56R will illuminate. If device 10 is too far away, the yellow LED 56Y will illuminate.

When green LED 56G illuminates, the operator knows that the distance is optimum and prepares to operate data storage switch 26. When the signals being returned from the material 36 have been converted to valid data, the green LED 60 will be illuminated. At this time, with LEDs 56G and 60 both illuminated, the operator can operate switch 26 to store the data, the satisfactory occurrence of which is indicated by the flashing illumination of green LED 58. Simultaneously with the storing of the data, the date and time of day will be recorded, together with the identifying "tag" entered by the operator via keypad 62.

As quickly as LED 58 lights to show the satisfactory storage of data, the thickness or density value of the material 36 will be displayed on digital display 54. The operator can choose to make a series of measurements at minimum intervals by holding switch 26 closed, or measurements can be repeated at wider intervals, as desired. It can be advantageous to use external braces, supports, tripods, etc., to assist in holding the device 10 steady over a material 36. Such supports are well-known in the art and do not form a part of the present invention. Further, while a prime consideration of a portable backscatter gauge constructed in accordance with various features of the system of the present invention is to make basis weight measurements without the need for contact with the material 36 being measured, it is well within the purview of such a device, either portable or non-portable, being herein described to provide a surface, such as skid plates 31, for example, which can contact, rest upon, and/or be supported by such material 36.

Figure 5:
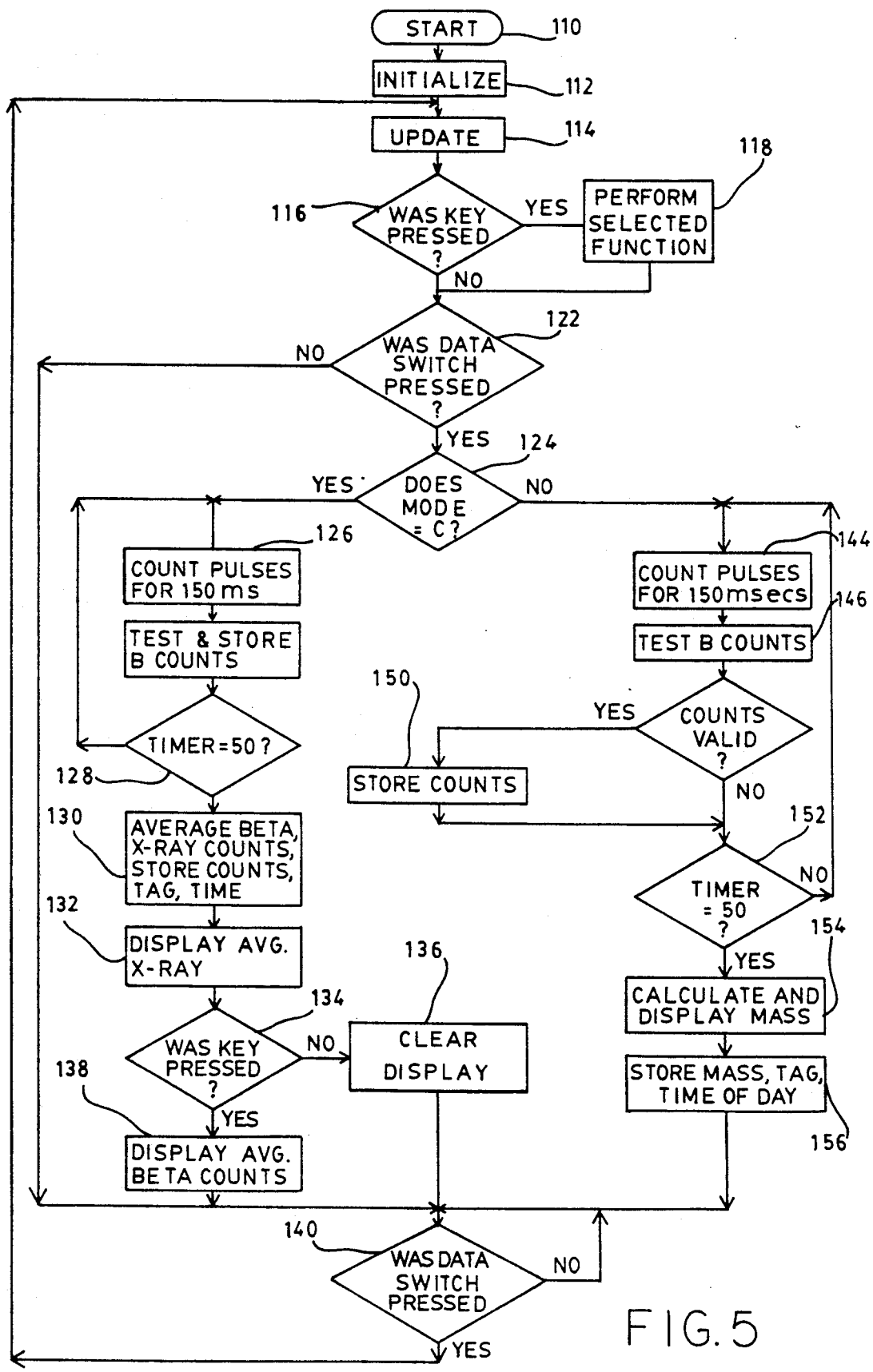
FIG. 5 is a flow chart diagram of the process of the electronic portion of the device of FIG. 1.

The internal operation of a device constructed in accordance with various features of the present invention is diagrammed in the simplified flowchart of FIG. 5, beginning with START at 110. The first step is to Initialize the dynamic components; the LEDs, the LCD, and the electronic circuits. This step is indicated by process box 112. Next, the Update step 114 reads the mode in which the device 10 was last used, which is stored in memory, and zeros all circuits.

Following the initialization step at 112, the process consists of a continuous loop, which starts with the Update step 114 just mentioned and continues by checking the keypad at decision box 116 for any entries. If any key was pressed, the function mandated is performed at box 118. After checking the keypad, the basic flow of the internal process is comprised of a sequence of steps controlled by the status of the data storage switch 26, as indicated by decision box 122. If the answer to the question of box 122 is "no", the function is transferred to decision box 140 where the device 10 simply waits until switch 26 is pressed, giving a "yes" answer at the output of decision box 140, returning the flow to the Update box 114. This time, the answer at decision box 120 is also "yes" which leads to decision box 122.

In the C (contacting) mode, the first step is shown at process box 124, which is to count the electronic signals representing the pulses of radiation being received by the detectors 40 and 48. At 126, the beta pulses are tested and stored. As indicated by decision box 128, these two steps are performed 50 times.

Next, at process box 130, the counts are averaged and stored, together with a tag entered by an operator and the time of day. The average X-Ray count is then displayed on the LCD 54 as indicated at process box 132. At decision box 134, the keypad 62 is checked to see if any key has been pressed. If no key has been pressed, the display 54 is cleared at 136 and the status of the data storage switch 26 is checked at decision box 140. If a key was pressed at 134, the average beta count is displayed at 138 and the status of data storage switch 26 is checked at decision box 140.

Returning to decision box 122, it will be seen that a Non-C mode condition leads to the step at 144 of counting the electronic signals representing the pulses of radiation received from a material 36 under surveillance. At process box 146, the beta counts are tested and, if valid, stored at process box 150. In either case, whether the counts are valid or not, the process is performed 50 times, as indicated by the timing counter decision box 152.

After performing the preceding steps 50 times, the mass figure is calculated and displayed at box 154, and stored at box 156, along with the operator's tag and the time of day. The next process step is again to check the status of the data storage switch 26 at decision box 140.

In every case where the process flow requires the choice indicated at box 122, a "no" answer puts the device in a "do-nothing" loop, waiting for the answer to change to "yes". When the "yes" answer is realized by the operating of data storage switch 26, the process returns to the input side of the Update box 114 and the entire process is repeated.

Thus, it will be seen that there has been provided a description of a portable backscatter gauge for measuring the density/thickness (called basis weight measurements) of sheet material without directly contacting the material, and without the errors introduced by relative motion between the device and the material, aging of radioactivity emitters, or obscuration of an emission window. This has been made possible through the utilization of two radiation effects, a first type or weaker radiation indicating primarily a distance factor between the radiating element and a material being measured, and a second type or stronger radiation indicating primarily a thickness/density (basis weight) factor of a material being measured.

While a preferred embodiment of a device constructed in accordance with various features of the present invention has been described herein, no attempt has been made to limit the device to such description.

Rather, such description has been intended to embody all possible variations and alternate constructions falling within the spirit and scope of the invention as defined in the appended claims.

Accordingly, this invention is limited only by the claims appended hereto, and their equivalents, when taken in combination with the complete description contained herein.

I claim:

1. A device for making basis weight measurements of sheet material under surveillance, comprising:
    at least one source of first and second radioactive emissions for irradiating said surveilled sheet material in such a manner that radiations of said first and second radioactive emissions impinge on said surveilled sheet material in a substantially identical solid angle of coupling therebetween;
    detecting means for detecting reflected portions of said first and second radioactive emissions reflected from said surveilled material, said detecting means serving to convert said reflected portions into first and second electrical signals, wherein said first electrical signal is representative of at least a factor of a distance between a surface of said device and said surveilled material in combination with a factor of said basis weight of said surveilled material, and said second electrical signal is representative of at least a further factor of said basis weight of said surveilled material in combination with a further factor of said distance factor;
    signal conditioning means wherein said first and second electrical signals are conditioned and separated into discrete distance and basis weight signals; and
    display means for displaying said discrete distance and basis weight signals to an operator.

2. The device of claim 1 wherein said first radioactive emission is a beta particle emission, and said second radioactive emission is an X-Ray emission.

3. The device of claim 2 wherein said beta particle emission is from Krypton-85, and wherein said X-Ray emission is from Americium-241.

4. The device of claim 1 wherein said at least one source of first and second radioactive emissions comprises any combination of isotopes of two different alpha, beta, gamma, and/or X-Ray emitting materials.

5. The device of claim 1 wherein said at least one source of said first and second radioactive emissions comprises different energy levels of radiation from a single radioisotope.

6. The device of claim 1 wherein said detecting means has energy resolution capabilities for producing said first and second electrical signals, whereby said first electrical signal is representative of energy of said first radioactive emission, and said second electrical signal is representative of energy of said second radioactive emission.

7. The device of claim 1 wherein said conditioning means has a memory portion and wherein said first and second electrical signals are stored in said memory portion of said signal conditioning means, and are capable of being transferred on command to said display means, said first electrical signal being used to illuminate distance related light emitting devices, and said second electrical signal being converted into a visible display of engineering units indicative of said basis weight of said surveilled material.

8. The device of claim 1 wherein said at least one source of said first and second radioactive emissions comprises an isotope of only one type of radioactive substance producing both beta and X-ray radiation.

9. The device of claim 8 wherein said isotope of said radioactive substance is Strontium 90.

10. The device of claim 1 further comprising a collimator through which said first and second radioactive emissions are directed for providing a substantially identical solid angle of irradiation by both said first and second radioactive emissions for irradiating a selected area of said material being surveilled.

11. A portable basis weight measurement device, having operator input means, and comprising:
    a first and second source of two different types of first and second radioactive emissions, the types and energy levels of said radioactive emissions being selected to accommodate basis weight measurement of a material to be surveilled;
    a first detector for detecting a reflected portion of said first radioactive emission from said first source reflected back from said material, said first detector serving to convert said reflected portion of said first radioactive emission into an electrical signal representative of the received strength of said reflected portion of said first radioactive emission;
    a second detector for detecting a backscattered portion of said second radioactive emission from said second source backscattered from said material, said second detector serving to convert said backscattered portion of said second radioactive emission into an electrical signal representative of the received strength of said backscattered portion of second radioactive emission;
    electronic signal conditioning and data processing means, having a time of day and date signal generating capability and a memory portion, for converting said first electrical signal into data representing a distance between said device and said surveilled material and for illuminating an appropriate light emitting device, and for converting said second electrical signal into data representing mass per unit area of said surveilled material, said data representing distance and said data representing mass per unit area being stored in said memory portion of said data processing means, together with signals from said operator input means and said time of day and date signals, and for converting said mass per unit area data into engineering units; and
    a recording device for display of said engineering units upon command from said operator input means.

12. The device of claim 11 further comprising a collimator through which said first and second radioactive emissions are directed for providing a substantially identical solid angle of irradiation by both said first and second radioactive emissions for irradiating a selected area of said material being surveilled.

13. The device of claim 11 wherein said first and second detectors have energy resolution capabilities for producing said first and second electrical signals, whereby said first electrical signal is representative of said energy level of said first radioactive emission, and said second electrical signal is representative of said energy level of said second radioactive emission.

* * * * *